(12) United States Patent
Hennemann et al.

(10) Patent No.: US 10,092,507 B2
(45) Date of Patent: Oct. 9, 2018

(54) IMPLANTABLE CELLULAR AND BIOTHERAPEUTIC AGENT DELIVERY CANISTER

(71) Applicants: NANOVAULT MEDICAL, LLC, St. Paul, MN (US); Willard W. Hennemann, Washington Crossing, PA (US); Bryan L. Steelman, St. Paul, MN (US); Thomas J. Webster, Barrington, RI (US)

(72) Inventors: Willard W. Hennemann, Washington Crossing, PA (US); Bryan L. Steelman, St. Paul, MN (US); Thomas J. Webster, Barrington, RI (US)

(73) Assignee: NanoVault Medical LLC, St. Paul, MN (US)

(*) Notice: Subject to any disclaimer, the term of this patent is extended or adjusted under 35 U.S.C. 154(b) by 2 days.

(21) Appl. No.: 15/530,067

(22) PCT Filed: Jun. 6, 2015

(86) PCT No.: PCT/US2015/000065
§ 371 (c)(1),
(2) Date: Nov. 30, 2016

(87) PCT Pub. No.: WO2015/187204
PCT Pub. Date: Dec. 10, 2015

(65) Prior Publication Data
US 2017/0319472 A1    Nov. 9, 2017

Related U.S. Application Data

(60) Provisional application No. 61/997,635, filed on Jun. 6, 2014.

(51) Int. Cl.
*A61K 9/00* (2006.01)
*A61M 39/02* (2006.01)
(Continued)

(52) U.S. Cl.
CPC .......... *A61K 9/0024* (2013.01); *A61K 31/337* (2013.01); *A61K 31/397* (2013.01);
(Continued)

(58) Field of Classification Search
CPC .. A61K 9/0024; A61K 31/337; A61K 31/397; A61K 31/436; A61K 31/65;
(Continued)

(56) References Cited

U.S. PATENT DOCUMENTS

| 5,201,728 A * | 4/1993 | Giampapa | A61K 9/0024 |
| | | | 424/424 |
| 6,471,689 B1 * | 10/2002 | Joseph | A61L 29/04 |
| | | | 424/424 |

* cited by examiner

*Primary Examiner* — Manuel Mendez
(74) *Attorney, Agent, or Firm* — Christopher & Weisberg, P.A.

(57) ABSTRACT

The invention relates to a metallic, nanoporous canister used to encapsulate cellular and/or biotherapeutic agents. The device is biocompatible and functions to wholly isolate a therapeutically active agent and/or cells therein. Their implantation, and survival in vivo, permits the local or systemic diffusion of their encapsulated cellular and/or biomolecular and therapeutics factors with the potential to promote repair of damaged or degenerated tissues in mammalian hosts, primarily humans.

19 Claims, 6 Drawing Sheets

(51) Int. Cl.
　　　*A61K 31/397*　　　(2006.01)
　　　*A61K 31/65*　　　(2006.01)
　　　*A61K 31/337*　　　(2006.01)
　　　*A61K 31/436*　　　(2006.01)
　　　*A61K 38/18*　　　(2006.01)
　　　*A61K 31/7036*　　　(2006.01)
　　　*A61K 38/14*　　　(2006.01)
　　　*A61K 39/395*　　　(2006.01)
　　　*A61K 38/22*　　　(2006.01)
　　　*A61K 35/28*　　　(2015.01)
　　　*A61K 47/02*　　　(2006.01)

(52) U.S. Cl.
　　　CPC ............ *A61K 31/436* (2013.01); *A61K 31/65* (2013.01); *A61K 31/7036* (2013.01); *A61K 35/28* (2013.01); *A61K 38/14* (2013.01); *A61K 38/1866* (2013.01); *A61K 38/22* (2013.01); *A61K 39/395* (2013.01); *A61K 47/02* (2013.01); *A61M 39/0247* (2013.01); *A61M 2039/027* (2013.01); *A61M 2039/0261* (2013.01); *A61M 2039/0276* (2013.01); *A61M 2205/04* (2013.01)

(58) Field of Classification Search
　　　CPC .... A61K 31/7036; A61K 35/28; A61K 38/14; A61K 38/1866; A61K 38/22; A61K 39/395; A61K 47/02; A61M 39/0247; A61M 2039/0261; A61M 2039/027; A61M 2039/0276; A61M 2205/04
　　　USPC ...................................... 604/288.02; 424/424
　　　See application file for complete search history.

IMPLANTABLE CELLULAR AND BIOTHERAPEUTIC AGENT DELIVERY CANISTER

FIELD OF INVENTION

The invention relates to a metallic, nanoporous device used to encapsulate cellular and biotherapeutic agents. The device is biocompatible and functions to wholly isolate a therapeutically active agent and/or cells therein. Their implantation, and survival in vivo, permits the local or systemic diffusion of their encapsulated cellular and/or biotherapeutic factors with the potential to promote repair of damaged or degenerated tissues in mammalian hosts, primarily humans.

BACKGROUND

The field of cellular and biotherapeutic agents research and development has provided novel, patient centric alternatives to resolving many chronic and costly disease conditions. Traditional pharmaceutical based therapies have yet to provide a cure for these often acquired and congenital conditions. These include the +100 autoimmune diseases affecting 50 million Americans (AARDA) such as Type 1 diabetes (T1D), Rheumatoid Arthritis (RA), Multiple Sclerosis (MS) and neurodegenerative diseases including Parkinson's and Alzheimer's disease. Typically for these disease states, cellular production of required biomolecular factors that direct normal physiological function are missing. Unfortunately, the unexplained destructive attack on normal cellular function by the body's own protective immune system is frequently the cause.

As an example, the most costly of these is Type 1 diabetes, a disease where the body's immune system attacks and destroys insulin producing β-cells in the pancreas. This disease, most frequently diagnosed in children, affects nearly 3 million Americans who require $15 billion in annual care, including $1.8 billion spent on insulin.

Cellular therapy offers the option of replacing lost or damaged cells with donor cells or stem cells capable of producing and secreting a steady supply of biomolecular factors. These biomolecular factors have the potential to restore lost or impaired physiological function within the mammalian host. For example, replacing lost islets of Langerhans has been shown to restore glucose transport in mammals with insulin-dependent diabetes. And dopaminergic neurons or neural stem cell-based therapy have been shown to reduce the effects of Parkinson's disease.

Biotherapeutic agents, or biologics, represent another novel therapy option. These biomolecular substances are derived from living organisms, where living tissues are made or modified to create therapeutic compounds. Insulin, used to regulate blood sugars, was the first medicine produced using biotechnological methods. Many biologics have been subsequently developed to treat chronic illnesses like cancer, anemia, multiple sclerosis, and rheumatoid arthritis. Such biologics also have the potential to disrupt unwanted physiological events, as in potent cancer compounds or anti-infectious disease vectors. These therapeutic and living tissue-derived and active factors include but are not limited to proteins, peptides, genes, antibodies hormones, growth factors and neurotransmitters.

Envisioned is a complementing site-specific delivery device such as a canister or tube platform with the potential for the long-term (>12 months) controlled secretion of these living tissue derived, biologically active and cell-based therapeutic agents.

A key to utilizing cellular and biotherapeutic agents is their transplantation into mammalian tissues. As a foreign biomaterial, they trigger the host's naturally protective immune system response, which compromises their ability to survive and function. Likewise, as living tissues, careful placement is required to avoid harmful side effects to the mammalian host. For example, current medical practice requires the patient to remain on life-long immunosuppressant drug therapy following the direct administration of foreign but therapeutic cells (e.g. injection) into an organ or tissue. This required concomitant therapy unfortunately carries significant risks including toxicity to both the host and the implanted cells and/or biotherapeutic agents. There is also the concern that certain cell types (e.g. pluripotent stem cells), although potentially therapeutic, carry the risk of differentiating and developing tumorogenicity. Additionally, blood-mediated inflammatory reaction (IBMIR) destroys a significant portion of cells when transplanted into the vascular system.

The sustained function of therapeutic cells and biotherapeutic compounds, especially when they trigger an aggressive immune response, require a specialized delivery canister alternative. The present disclosure describes an implantable, canister-like "platform" for sustained biomolecular agent-based therapies. Envisioned are a variety of specialized implantable canisters for delivering cells and biotherapeutics in vivo that address the following requirements; (1) are biocompatible and well tolerated by the mammalian host, (2) protect the delivered materials from immune response and rejection; (3) establish an environment that supports targeted cellular function and biotherapeutic activity; (4) allow for the continuous diffusion of their specific biomolecular factors for treating disease conditions; (5) complement current medical practice associated with implantable devices (e.g. post-implant visualization, infection control, retrieval, mechanically and structurally robust, sterility, etc.).

Likewise, such a device delivery can potentially obviate problems associated with current cell and biotherapeutics delivery canister-based approaches:

1) The implantable device (e.g., canister) utilizes medical grade metal materials that are well tolerated by the body and are biocompatible. Metal device manufacturing is a mature technology and applied across a variety of implanted medical devices like pacemakers, orthopedic implants, cardiovascular stents, etc. Existing processes and treatments render these materials to be clean, passive, corrosion resistant, mechanically stable and biocompatible by way of processes such as chemical cleaning, etching, electropolishing and acid passivation. Specific metals are known to have a protective oxide layer that renders surfaces relatively inert. This results in modest surface charges that minimize protein deposition in situ, curtail monocyte and macrophage adhesion. The metals materials characteristic results in generally low levels of (acute) inflammation, thus minimizing aggressive fibrotic encapsulation resulting from chronic inflammation and foreign body response. Currently available cell and biotherapeutic devices are pouch-like macroencapsulation constructs. They are constructed from multilayered polymer materials. Such implanted polymers are known to trigger untoward inflammatory reactions, primarily because of impurities inherent with their manufacture (e.g. catalysts, binders, monomers, initiators). Of additional concern is the lingering toxicity of these manufacturing impurities and their effect on the encapsulated cellular and/or biotherapeutic agents and their secreted therapeutic factors;

2) The metallic implant device can be made into a variety of shapes and sizes, whose physical characteristics can be crafted to meet specific clinical therapeutic requirements while offering superior structural integrity. Delivery pouches constructed of polymeric materials are limited in the variety of possible constructs when compared to metal based designs. Their designs incorporate layered elements including microfiber filters, webbing, spacers, shims, etc., making them prone to splitting, fracture, buckling and ballooning. Additionally, polymeric macroencapsulation delivery pouches contain undesirable artifacts associated with their manufacture. These manufacturing defects, such as sharp edges, inconsistent layered materials deposition, and poor edge seals, can cause implant site irritation, resulting in untoward inflammation and aggressive tissue reaction. They are known to cause significant scar tissue formation (fibrosis) that envelops the device, making it nonfunctional. They are known to disfigure and often kind following their implantation.

To the contrary, metals based medical device manufacturing processes have been refined and eliminate such artifacts. They can be manufactured as a single material construct, with defined wall and overall device thickness. As a single materials construct, there is no need for layered elements. Anatomically appropriate features (e.g. rounded features, increased surface area refinements) are easily incorporated into the superstructure. Additionally, the nature of metal materials in medical applications is well documented and understood in terms of strength, durability, resistance to corrosion and wear. Similarly designed polymer devices generally fall short with regard to these important features when placed in normal physiological stresses and conditions;

3) Nanoscale through-porous manufacturing processes permit control over pore size, pore density and morphology. Tailored pore sizing is a key criterion for the continuous diffusion of specific biomolecular factors for treating disease conditions. These biomolecular factors, most of which are considered to be small molecules, must freely exit from the delivery canister, exiting into the surrounding tissues of the mammalian host. Likewise, this tailored porous dimension can withstand the host's cell-mediated immunity, mechanically blocking immunocytes and their secretory immunoglobulins (IgM and IgA) and macrophages accessing the canister content. Methods for manufacturing such tailored nanoscale porous structures in metal include electrochemical dealloying at the atomic level, nanoparticulate fusing resulting in porous morphologies between metal particles and/or nanophase templates derived from block-co-polymer and block-co-metals. These processes can be used singularly or in combination. Important to these modification processes is the necessity of bicontinuous morphology. This nanophase materials outcome allows for controlled biomolecular factor secretion, necessary for any closed-looped delivery where factor release (e.g. timing) is an important therapeutic variable;

4) Nanotechnology derived materials significantly change metal properties by controlling the atomic, molecular, and supramolecular levels of the canister. These nanophase porous metal manufactured materials, especially at the surface, offer several physiological benefits. Due to the presence of numerous nanostructures (e.g., proteins) in the body, cells are accustomed to interacting with surfaces that have a large degree of nanometer roughness. Despite this fact, many current synthetic polymer delivery pouches possess conventional (micron-sized) surface features only.

It is well documented that manufactured materials with nanophase implant surfaces can:
Alter implant surface energy; in certain scenarios, they act to camouflage (endothelialization) and in others, they selectively deter (retard inflammatory cells response).
Control initial protein adsorption and bioactivity
Promote cellular activity/growth while inhibiting infection and chronic inflammation
Provide increased drug loading and prolonged drug delivery In the specific application to the envisioned delivery canister, the incorporated nanophase porosity will lead to increased vascular endothelial cell proliferation, important for therapeutic factor uptake from the enclosed therapeutic agents.

Internal to the canister, the large surface to volume ratio will optimize the exchange of nutrients, oxygen, and removal of waste metabolites, thus increasing the rates of factor release and responsiveness changes in the surrounding tissues. This approach—of utilizing defined nanophase regions within the same metal construct—would allow contained biomolecular factors to reside, via varied porosity, closer to the external, vascularized surface of the canister without having to greatly diminish the canister's wall thickness and thus maintaining the required structural integrity of the delivery canister. Such internal nanophase structures that provide for improved cell adhesion to the device super-structure would facilitate phenotypic control and cell survivability.

External and at the canister to tissue interface, nanophase modified surface textures could be used to facilitate use of anti-inflammatory, antibiotic and anti-fibrotic compounds to retard immediate foreign body responses while allowing for surface only imbedded vascularization agents for enhanced biomolecular factor survival and their long-term function of secreted therapeutic agents.

DETAILED DESCRIPTION

Definitions

"Bicontinuous Morphology" refers to at least two regions, each of substantially uniform composition which differs from the other and each of which forms a continuous pathway from one surface of an article to another surface of an article. Thus, a bicontinuous morphology will have two continuous pathways or two sets of continuous pathways extending from one surface of the material to the other surface.

"Metabolically Active" means cellular or biotherapeutic agents that produce therapeutic metabolites in a biologically relevant environment.

"Nanoporous" means very small pores extending through a surface, and measured in increments of a millionth of a meter or as $10^{-9}$ of a meter (abbreviated "nm").

"Nanoscale" and "nanophase" means measurements in increments in increments of a millionth of a meter or as $10^{-9}$ of a meter (abbreviated "nm").

"Rigid" means stiff and not bending.

"Through-porous membrane" means a semipermeable membrane, also termed a selectively permeable membrane, a partially permeable membrane or a differentially permeable membrane, is a type of biological membrane that will allow certain molecules or ions to pass through it by diffusion and occasionally specialized "facilitated diffusion" along with other types of passive transport and active transport.

Nomenclature
10 First Nanoporous Region
120 Second Nanoporous Region
100 Canister
102 First Major Surface
104 Second Major Surface
106 Side Surface
108 Port
108a Extended Silicone Tube
110 Internal Barrier
112 Interior Chamber
212 Internal Channel
300 Canister
308 Port
400 Canister
408 Port
412 Internal Channel
500 Nanoporous and Patterned Surface
600 Nanoporous and Patterned Surface
700 Nanoporous and Patterned Surface
800 Nanoporous and Patterned Surface
900 Nanoporous and Patterned Surface
1000 Nanoporous and Patterned Surface
1100 Nanoporous and Patterned Surface
1400 Canister
1402 Outer Metallic Canister
1404 Inner Polymeric Pouch
1406 Port
1500 Canister
1502 First Major Surface
1504 Second Major Surface
1506 Side Surface
1508 First Sealed Chamber
1510 Second Sealed Chamber
1512 Third Sealed Chamber
1514 Fourth Sealed Chamber
1516 Fifth Sealed Chamber
1518 Sixth Sealed Chamber A platform for cellular and biotherapeutic agent delivery in a mammalian host, primarily humans, utilizing an implantable metal canister is described herein. Such a cell and biotherapeutics delivery canister provides a suitable environment for the cells and biotherapeutics to survive and function (e.g. produce and secrete therapeutic bioactive factors) without adversely affecting the mammalian host recipient or impaired by normal immunoprotective response.

The cell and biotherapeutics delivery canister construct is made of medical-grade metal(s). In its simplest configuration, it is a metallic canister composed of two identical cup-shaped halves to create a hollow chamber. The medical-grade metals are modified to contain a nanoscale through-porous and bicontinuous membrane morphology. The internal void chamber of the envisioned canister is accessed through an incorporated silicon septum or attached infusion tube built into the canister, also sealed with a silicon septum for needle injection.

The metals material is processed in a way that to create a porous, membrane-like structure. This modification takes place at the nanoscale level. The nanoscale pore size is sized and exacted to control bioactive factor exchange and diffusion. Specifically, a tailored nanoscale, through-porous feature with bicontinuous morphology within the canister superstructure allows for highly controlled therapeutic factor diffusion, both in and out of the delivery canister. The pore sizes range from approximately 20 nm to 5000 nm with a wall thickness of 5 to 250 microns. The wall thickness can be varied to provide a balance between efficient diffusion and structural integrity of the implanted device.

The incorporated and tailored membrane also precludes certain unwanted biomaterials from penetrating the implanted delivery canister and contacting its therapeutic agent contents. These include immunogenic factors (e.g. immune cells or immune agents). The pore sizes may range from approximately 20 nm to 5000 nm with a wall thickness of 5 to 250 microns. The wall thickness can be varied to provide a balance between efficient diffusion and structural integrity of the implanted device.

Nanophase biofunctional surfacing of implanted devices has been shown to match the recognition ability of biological systems, especially microvascularization. As such, topographic patterns can be executed on the canister delivery surface to match proteins at the nanometer scale and cells at the micrometer scale. The pore size feature of the canister superstructure metal material will facilitate desired vascular tissue incorporation of the canister to aid in the survival and/or function of its contents. The pore sizes may range from approximately 20 nm to 5000 nm with a wall thickness of 5 to 250 microns. The wall thickness can be varied to provide a balance between efficient diffusion and structural integrity of the implanted device.

The availability of vascular supply to the encapsulated therapeutic agents relates to their survival and function. A constant supply of oxygen, nutrients, and waste removal are required for nourishing the implanted cells and maintaining an optimal environment within the delivery canister for their longevity. In the case of therapeutic cells, a well-vascularized environment prevents death or damage through the effects of ischemia or hypoxia. The nanoscale texturing of the external surface of the delivery canister will encourage growth of vascularized tissue into the porous construct of the device. At the same time, scar tissue formation, triggered by a foreign body response, is mitigated. The desired ingrown vascular tissues also stabilize the implant canister, preventing its translocation into other body regions or tissues.

Nanoscale texturing of the internal void surface of the canister device will encourage distribution of therapeutic contents within the canister to the outermost regions of the delivery canister. This will encourage more immediate access to the vascularized tissues resident to the outer surface of the canister device, resulting in a large surface to volume ratio associated with nanophase materials construction.

The implanted delivery canister, having as well a nanoporous external surface, can be coated with an approved antibiotic compound to minimize infections. The porous surface texture of the delivery canister can be tailored at the nanoscale level for specific retention and release of such pharmaceutical agents. Representative antibiotics alone and in combination, include but are not limited to ampicillin, tetracycline, nafcillin, oxacillin, cloxacillin, dicloxacillin, flucloxacillin, vancomycin, gentamicin, streptomycin, erythromycin, penicillin, amoxicillin, sulfonamides and derivatives and analogues thereof.

The implanted cell and biotherapeutics delivery canister, having a nanoporous external surface, can be coated with approved antifibrotic drugs to inhibit the formation of unwanted fibrous tissues. The porous surface texture of the delivery canister can be tailored at the nanoscale level for retention and release of such pharmaceutical agents. Antifibrotic agents alone and in combination may include but are not limited to paclitaxel, everolimus, tacrolimus, rapamycin, and derivatives and analogues thereof.

The implanted cell and biotherapeutics delivery canister, having a nanoporous external surface, can be coated with approved biological or pharmaceutical agents (e.g. growth factors) to stimulate tissue in-growth and angiogenesis. The porous surface texture of the delivery canister can be tailored at the nanoscale level for retention and release of such pharmaceutical agents. Such biological or non-biological agents, alone or in combination, stimulate tissue incorporation and angiogenesis include but are not limited to PDGF (platelet-derived growth factor), VEGF (vascular endothelial growth factor), FGF-1 (fibroblast growth factor), endoglin, ephrin, plasminogen activators, angiogenin and derivatives and analogues thereof.

Functionality of the envisioned cell and biotherapeutics delivery canister is also based on proper dimensions of the delivery canister as they relate to particular cells, biotherapeutic volumes and clinical indications. Overall canister thickness, individual canister wall thickness, contour, shape, and the ability to load and recharge are important to sustaining a therapeutic number of cells for their ongoing survival and effect. The delivery canister shape must be anatomically convenient and non-protruding while meeting patient comfort and aesthetic considerations. In addition to size and shape, the metal material can be finely finished to avoid sharp traumatic edges. There may also be a clinical need to ultimately remove the delivery canister.

Another embodiment of the cell and biotherapeutics delivery canister includes multiple divided, internal chambers within the canister. These can either be connected or separate depending on septal or cell infusion tube access to the crafted, internal chambers. This embodiment would for example, facilitate the delivery of multiple biotherapeutic compounds where phased delivery is critical to therapeutic endpoints. This phased delivery would be dependent upon size of these internal chambers and location of sized nanoscale through-porosity.

Specifically important to cell survival is the ability to control cell distribution within the canister as cell clustering can impact their survival. Cell quantities can be positioned and controlled within the chamber utilizing internally crafted structures such as interconnected channels.

In all embodiments, the cells are loaded using needled injection through either a septum or self-sealing infusion tube that is designed for needle injection. In one embodiment, the septum is made of a self-sealing medical grade silicone. The septum is positioned to one side of the delivery canister, thereby facilitating manual palpation when implanted in subcutaneous tissues. Deeper tissue placement will utilize a defined tube length and a self-sealing tube with an access port that facilitates needle injection. This self-sealing tube can be brought to the exterior of the patient's body in conjunction with surgical placement and standard wound closure.

The method for loading cells first requires fixating the cell and biotherapeutics delivery canister in the mammalian host body. As such, the nanoporous through-porous membrane of the delivery canister is infiltrated with vascular and connective tissues. Once the cell and biotherapeutics delivery canister is encapsulated in a vascularized collagen matrix, delivering a cell and/or biotherapeutic agent is executed via needle injection, either through the built-in silicon septum or through the self-sealing access tube, which is connected to the delivery canister.

Throughout the disclosure, the terms cell and biotherapeutic infusion and cell and biotherapeutic transplantation are used interchangeably.

A transplanted cell and biotherapeutics delivery canister for containing therapeutic cells and biotherapeutics in vivo, in a mammalian host, is provided. The envisioned implanted cell and biotherapeutics delivery canister comprises a nanoporous canister that can be configured to create a hollow void chamber that is accessed for cell and biotherapeutic loading by way of syringe injection.

Metallurgists have specifically graded metals for clinical applications with enhanced characteristics that make them highly compatible within living tissues. Included in this list are medical-grade metals. Examples of such biomedical grade metals and alloys include stainless steel based alloys, cobalt-chromium based alloys, alloys and nickel-titanium based alloys. More recently platinum containing alloys have been perfected for intravascular applications.

The porous canister is formed of a biocompatible medical grade metal material that elicits only a mild inflammatory response in the body. The nanophase porous exterior portion of a through-porous membrane stimulates microvascular vessels to enter the cell and biotherapeutics delivery canister and promotes a vascularized collagen matrix to envelop the device, while curtailing a significant inflammation of tissues surrounding the delivery canister. The pore size and density of the nanoscale porous canister through-porous membrane encourages the growth and maintenance of these healthy vessels, which relate to the survival and targeted function of the therapeutic agents (e.g. molecular factor diffusion) contained within the delivery canister.

The required size of the porous canister depends on the optimal surface area-to-volume ratios for holding metabolically active agents in vivo and for ensuring their long-term survival within the vascularized void chamber(s). The number of chambers in the implanted delivery canister is determined by the volume and/or number of cells and/or biotherapeutics that are to be transplanted. The total volume of the cell and biotherapeutics delivery canister can be adjusted by increasing or decreasing the number of chambers and the optimum surface area-to-volume ratio of each individual chamber. The length, width and height of the chambers are also defined and manufactured to meet total therapeutic volume requirements.

Method of Using

The cell and biotherapeutics delivery canister disclosed can be implanted using standard surgical techniques. Applied surgical implantation can occur at the following anatomical locations: subcutaneous, intraperitoneal including the omentum, intramuscular, intravascular, intraocular, intracerebral or other appropriate sites including the digestive tract, spinal cord area or any other organ as required to elicit a therapeutic factor from implanted cells or biotherapeutic agents.

The loading procedure is a two-step process comprising a cell and biotherapeutics delivery canister being implanted and then followed by agent transplantation. After an in vivo incubation period during which the implanted cell and biotherapeutics delivery canister is infiltrated with a vascularized collagen matrix, the agent infusion step is then executed. The desired incubation period is generally thirty days to allow for angiogenesis and collagen infiltration of the porous canister. The incubation period may vary, depending on the extent of desired neovascularization and tissue formation. For example, the device may vascularize at different rates depending on the cell and biotherapeutics delivery canister material, dimensions, or coatings (e.g. antibiotic/antifibrotic coatings, growth factors, vascularizing agents etc.). There may be different vascularization rates pending locations in different body cavities and tissues. A clinically prepared expert can determine the appropriate incubation period while applying imaging tools that can help measure the extent of connective tissue deposition around and through the walls of the porous implanted canister.

For the metabolically active agent step, the implantation site is generally identified and needle accessed following (subcutaneous) palpation or a small surgical incision for deep tissue access. Specifically, the clinican will identify the septum built into the surface of the delivery canister. The cell and/or biotherapeutic agent is then delivered via needle injection through the incorporated silicon septum or self-sealing infusion tubing (e.g. polyethylene tubing) or any other suitable material to deliver the therapeutic agents into porous chamber of cell and biotherapeutics delivery canister during the agent infusion step. The number of septum or infusion tubes in the delivery system may correspond to the number of porous chambers. Deep tissue placement and access will likely involve image-guided technology commonly used in other medical device implant procedures. As a metallic device, medically accepted imaging is readily enhanced.

It is also envisioned that the delivery canister is placed along with the therapeutic agent using a single step and thus implanted together. The potential need exists for a biodegradable polymer coating for short-term containment of the encapsulated cell and biotherapeutic agent during such a singular implant procedure to control leakage loss of the molecular factors within the porous canister.

Construction

A void and porous canister may be created, for example, by joining (e.g.welding) the top and bottom halves of the canister along an edge. This would result in the canister being a single void chamber for holding the desired therapeutic agent. Its overall dimensions will generally be defined by the volume requirements and targeted anatomical location. In most embodiments the preferred delivery canister will measure 2-10 cm in length, 2-8 cm in width and have a height of 0.5 mm-5 mm.

Different iterations of this device include similarly parallel halves with patterned gross textures. These geometric patterns, such as wave patterns, circular divots or indents, ridges, grooves and other roughened or contoured surfaces would aid in increasing the desired maximum surface area for enhanced cellular and biotherapeutic factor exchange and vascularization.

As an implantable medical device, the cell and biotherapeutics delivery canister is sterilized using standard techniques prior to implantation. These include ethylene oxide, gamma radiation, cold plasma or dry heat autoclaving. The type of sterilization method used is dependent on the canister material. The cell and biotherapeutics delivery canister may be packaged in a self-seal package or any other sterilizable package along with a sterility indicator strip.

The disclosed delivery canisters can be used for transplantation of any cells, or a combination of cells, any biotherapeutic agent or combination of agents into a mammalian host body for providing therapeutic factors to the mammalian host for the treatment of a disease condition. Allogeneic, xenogeneic or syngeneic donor cells, patient-derived cells, including stem cells, cord blood cells and embryonic stem cells are appropriate for such transplantation. Living tissue derived and active factors include but are not limited to proteins, peptides, genes, antibodies hormones, growth factors and neurotransmitters.

Figure 1:
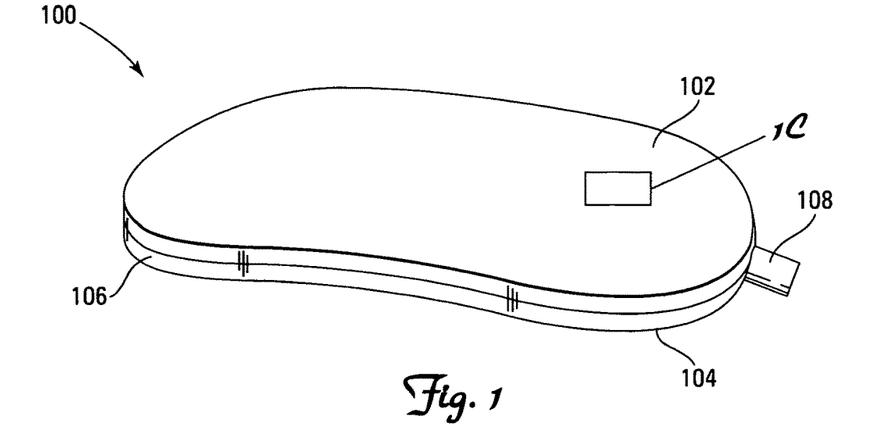
FIG. 1 shows a perspective view of an embodiment of the finished implant device, in this view, a canister.
Figure 1A:
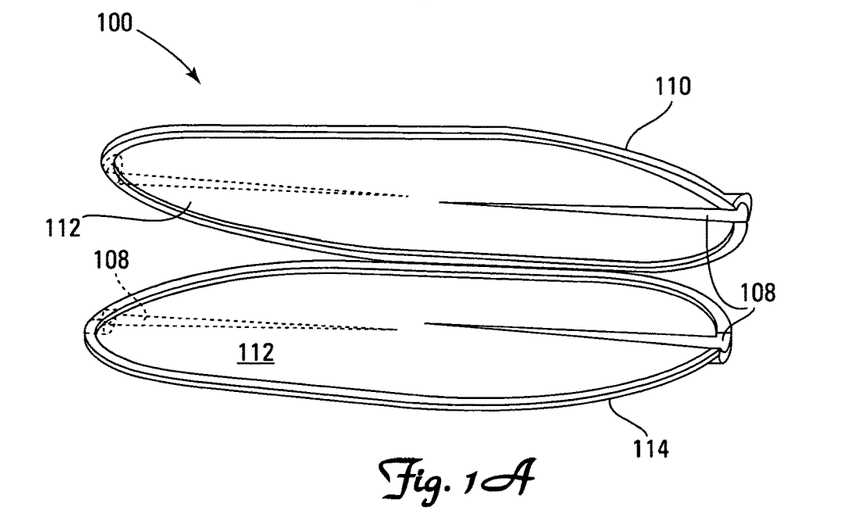
FIG. 1A shows a perspective view of the embodiment shown in FIG. 1, where the two shell members are opened.
Figure 1B:
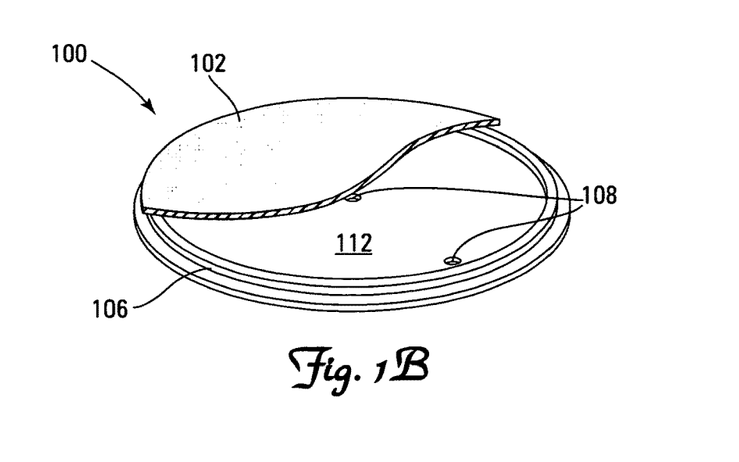
FIG. 1B shows a cut away embodiment of the canister containing no internal raised structure.

FIG. 1 shows an implantable canister 100 defining a first major surface 102, second major surface 104 and a side surface 106. A port 108 extends from the side surface 106, allowing access to the interior chamber 112 for infusion or flushing. FIG. 1A shows the canister 100 prior to being sealed shut, including an interior chamber 112 formed by combining both the upper shell 110 and lower shell 114. FIG. 1B shows the canister 100 with one the upper shell 110 cut away, showing the interior chamber 112. In all embodiments, the major surfaces can be fitted and/or joined and/or welded along an edge of the joined top and bottom halves, creating a single delivery canister.

Figures 1C, 2, 2A:
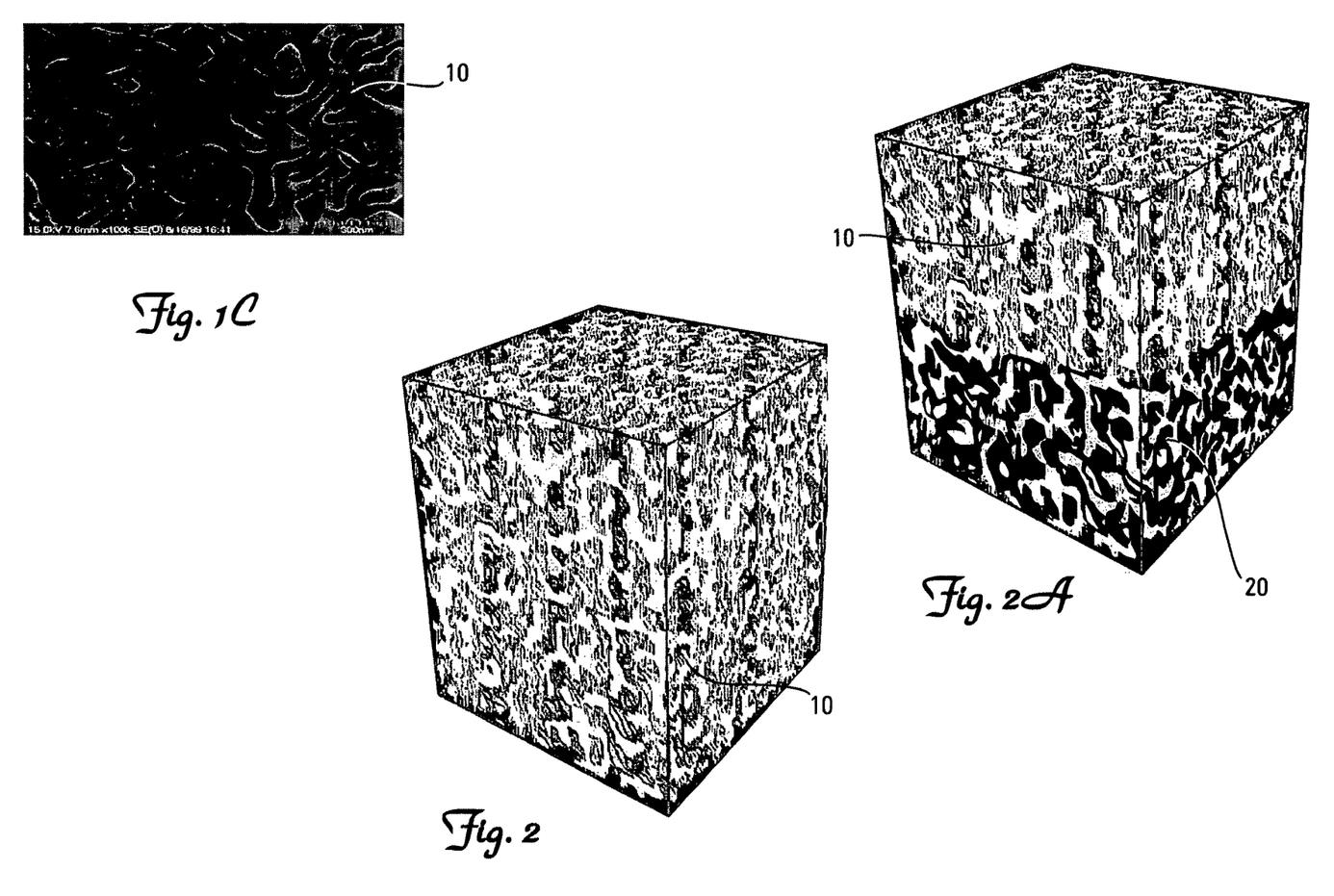
FIG. 1C illustrates a microscopic view of a metallic material with the nanoporous bicontinuous through-porous membrane morphology incorporated into the super-structure of the canister.
FIG. 2 shows an embodiment of a metallic material used to construct the invention showing a single nanoporous bicontinuous, through-porous membrane morphology structure.
FIG. 2A shows another embodiment of a metallic material used to construct the invention showing two interconnected layers of nanoporous, through porous membrane morphology structures.

FIG. 1C corresponds to the area shown on the first major surface in FIG. 1A and illustrates a microscopic view of the nanoscale through-porous membrane structure 10 of the canister 100. FIG. 2 illustrates a microscopic view of the s nanoscale through-porous metallic membrane material of the canister 100, 300 400, 1400, 1500 having a uniform or homogeneous nanoporous structure. FIG. 2A shows similarly illustrates a microscopic view of the metallic material of the canister 100, 300, 400, 1400, 1500 that is processed to possess an interconnected bicontinuous morphology which containing two distinct porous regions 10, 20, each of substantially uniform composition which differs from the other and each of which forms a continuous pathway from one surface of an article to another surface of an article.

Figure 3:
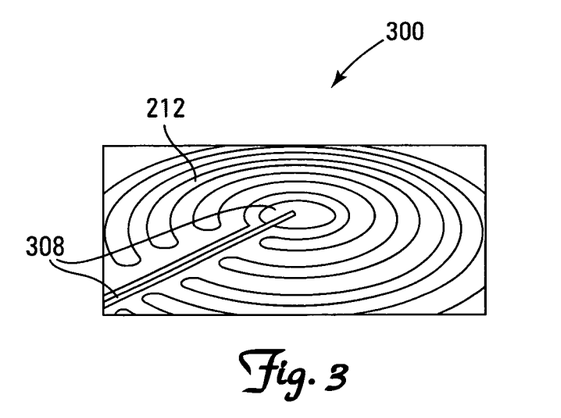
FIG. 3 shows another embodiment of the invention wherein the device is circular shaped having internal circular channels, wherein the channels are formed from a continuous, raised protrusion.
Figure 4:
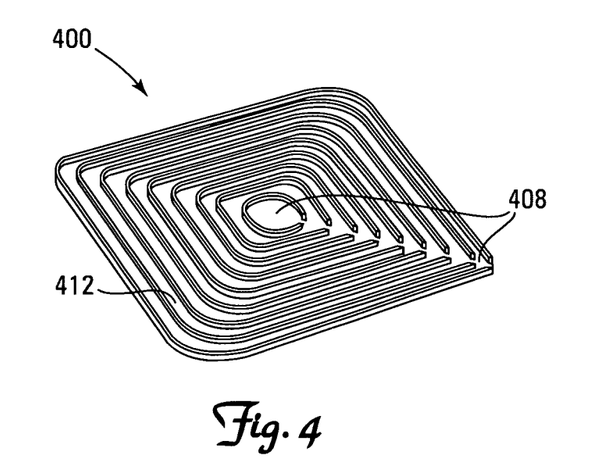
FIG. 4 shows yet another embodiment of the invention wherein the device is square shaped having internal square channels, wherein the channels are separate from each other.
Figure 5:
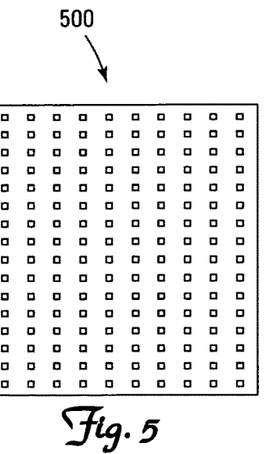
FIG. 5 shows a nanoporous surface pattern to increase internal and/or external surface areas to which a nanophase through-porous porosity is then applied.
Figure 6:
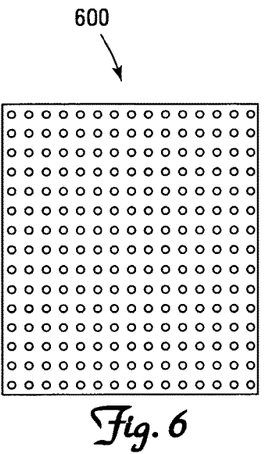
FIG. 6 shows an alternative surface pattern to increase internal and/or external surface areas to which a nanophase through-porous porosity is then applied.
Figure 7:
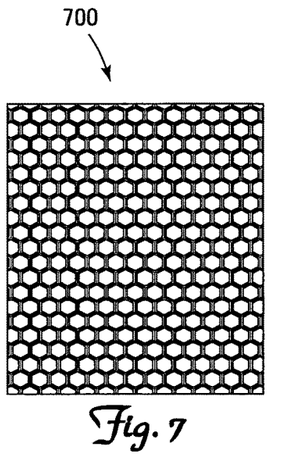
FIG. 7 shows another surface pattern to increase internal and/or external surface areas to which a nanophase through-porous porosity is then applied.
Figure 8:
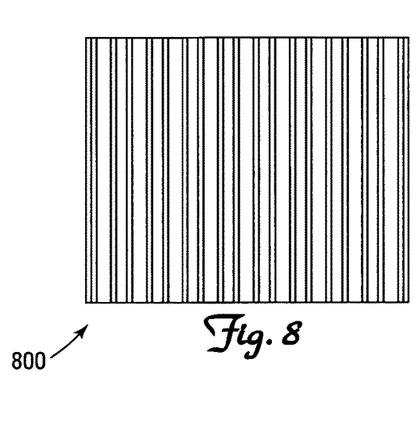
FIG. 8 shows yet another surface pattern to increase internal and/or external surface areas to which a nanophase through-porous porosity is then applied.
Figure 9:
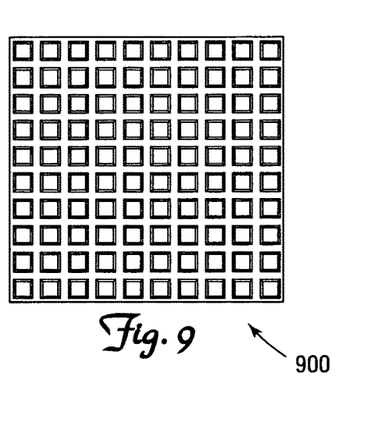
FIG. 9 shows a different surface pattern to increase internal and/or external surface areas to which a nanophase through-porous porosity is then applied.
Figure 10:
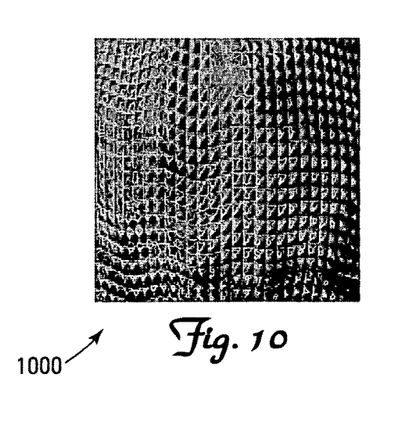
FIG. 10 shows another surface that is configured to display composite bends to increase internal and/or external surface areas to which a nanophase through-porous porosity is then applied.
Figure 11:
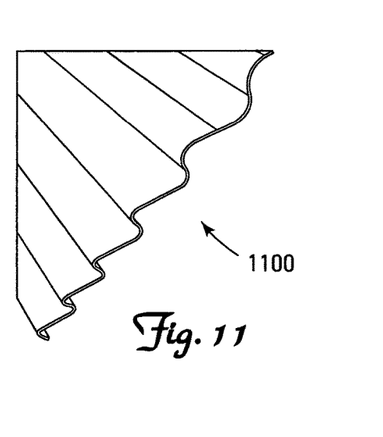
FIG. 11 shows another surface pattern to increase external and/or surface areas to which a nanophase through-porous porosity is then applied.

FIG. 3 shows a cut away view of a canister 300 configured to have an internal curved, raised pattern formed by an internal barrier 212 to physically stabilize a biotherapeutic agent (not shown) encased within. FIG. 4 similarly is a cut away view of an embodiment of a canister 400 having a squared shape with a plurality of raised internal barriers 412 to physically stabilize a biotherapeutic agent (not shown) held by the canister 400. FIGS. 3 and 4 are shown for purposes of illustration only and are not intended to be limiting as variations of shape and internal barrier configuration within a canister are infinite.

FIGS. 5-11 illustrate exterior nanoporous surface treatment patterns 500, 600, 700, 800, 900, 1400, 1500 that could be formed into the exterior and/or interior surface (unnumbered) of the canister 100, 300, 400, 1400, 1500. The purpose of the different exterior and/or interior nanoporous surface treatment configurations is to increase the surface area of the canister 100, 300, 400, 1400, 1500 to allow improved inflow and outflow which positively affects the output of cellular and/or biotherapeutic agents contained in the canister and diffused from the canister. FIGS. 5 to 11 are shown for purposes of illustration only and are not intended to be limiting as surface treatment variations of canister surface are infinite.

Figure 12:
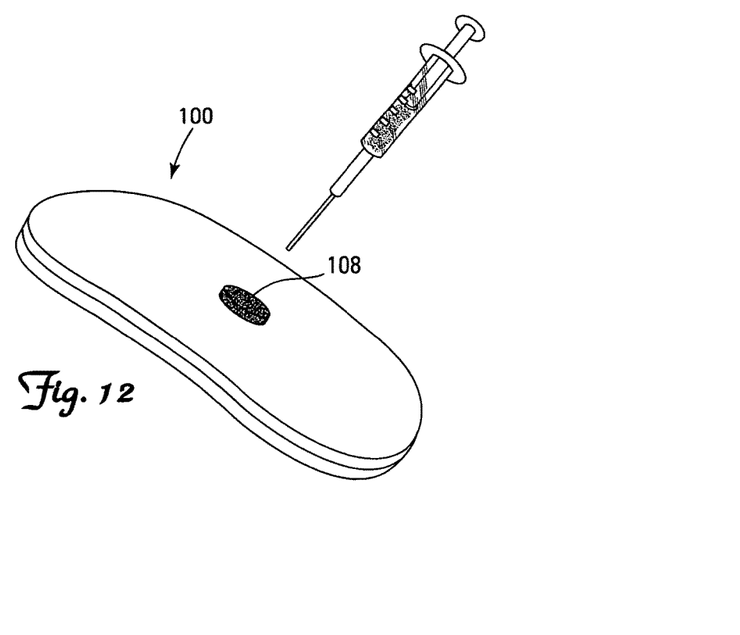
FIG. 12 shows a perspective view of the canister having a centrally located port to allow flushing or injection into the interior chamber of the canister.
Figure 13:
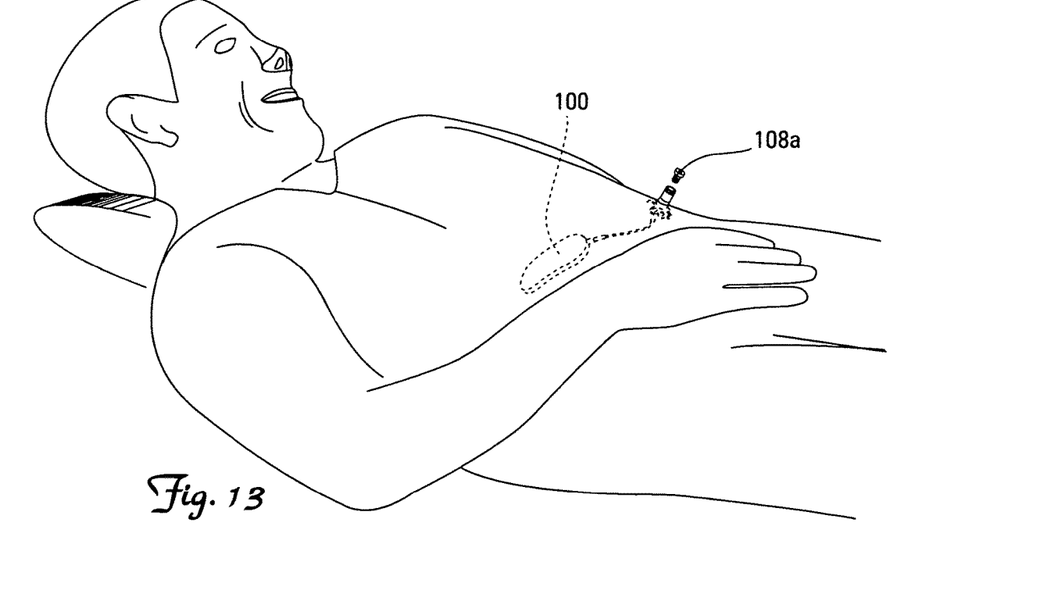
FIG. 13 shows a perspective view of the canister with a port system comprising an infusion tube used to allow flushing or injection into the interior chamber of the canister.

FIG. 12 illustrates the canister 100 being loaded through its port 108 with a biotherapeutic agent. FIG. 13 similarly illustrates a canister 100 having an extended tube 108a between the canister 100 and the exterior of a patient's body to allow loading of biotherapeutic agent (not shown) following a deep body (e.g., abdominal) implantation.

Figure 14:
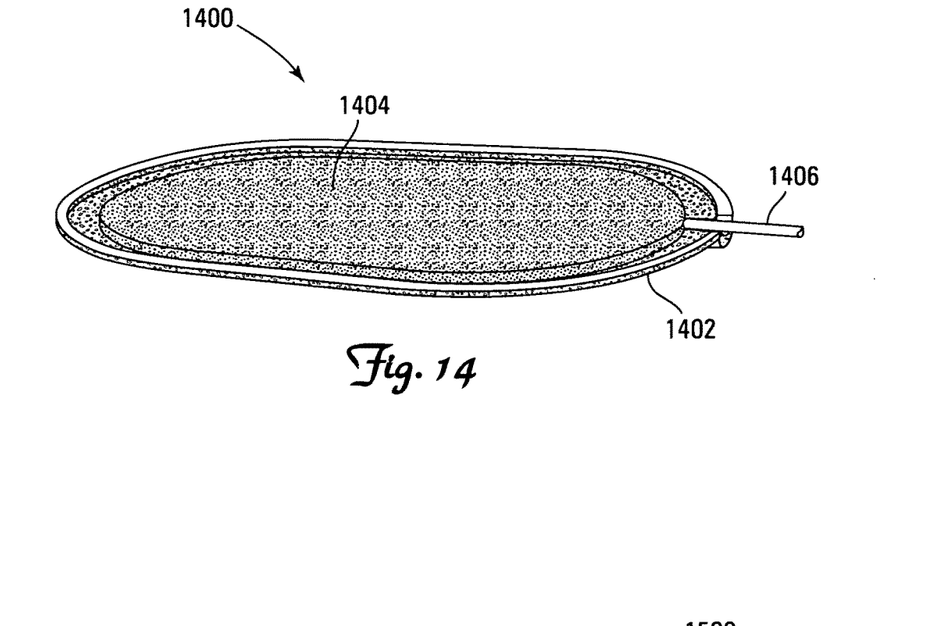
FIG. 14 shows a perspective, cut-away view of the outer one-half of a protective metallic canister with its nanophase through-porous membrane and encasing an inner porous polymeric pouch with a port for injecting biotherapeutic and/or cellular agents.

FIG. 14 is a view of a metallic nanoporous outer protective canister 1400 with an inner polymeric pouch 1404 constructed of a semi-permeable material and containing biotherapeutic agent (not shown). The outer protective canister 1400 is constructed of a nanoscale or microscale through-porous membrane to facilitate cellular or biotherapeutic agent diffusion. The polymeric pouch 1404 is provided fluid communication by means of extended silicone tube 1406.

Figure 15:
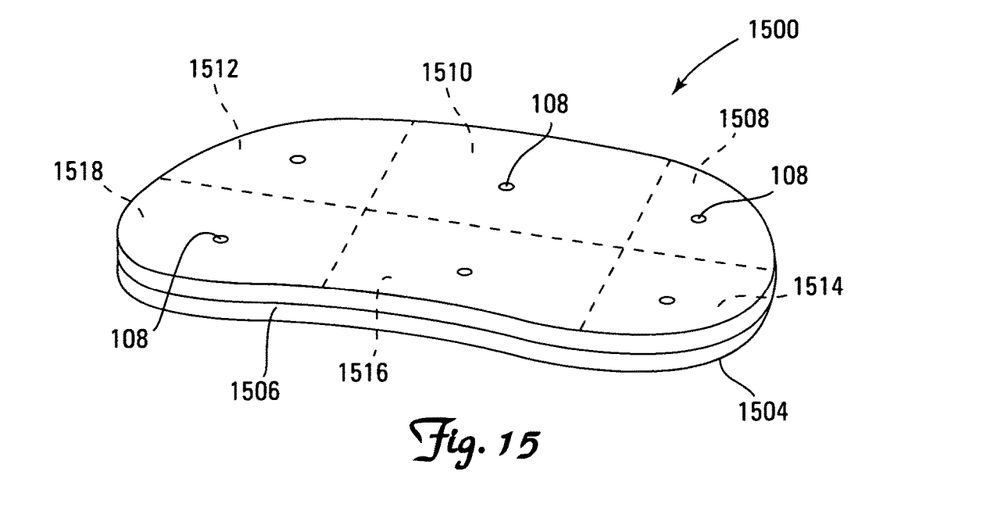
FIG. 15 shows an alternative of the canister with its nanophase through-porous membrane and having multiple sealed chambers and a plurality of ports.

In another embodiment, as shown in FIG. 15, the delivery canister 1500 is composed of multiple individual and independent chambers 1508, 1510, 1512, 1514, 1516, 1518. Each individual and independent chamber is accessed through its own port 108. Each independent chamber can have the same or varied nanophase through-porous membrane structure 10, 20 for controlled diffusion of various cellular or biotherapeutic agents, thus allowing sequenced delivery.

Other embodiments of the cell and biotherapeutic delivery canister will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An implantable canister for containing and delivering metabolically active agents, comprising:
    a metallic shell having nanoscale through-porous membrane characteristics including a bicontinuous morphology defining a first major surface, a second major surface, and an interior chamber between the first major surface and second major surface; and
    means allowing fluid communication with the interior chamber.

2. The canister of claim 1 further comprising the nanoscale through- porous membrane morphology having a range between approximately 20 nm to 5000 nm, wherein nutrients, oxygen and metabolites are efficiently exchanged and supports canister vascularization when implanted.

3. The canister of claim 1 wherein the metallic material is selected from the group consisting of cobalt-chromium based alloys, platinum based alloys, titanium based alloys, nickel-titanium based, nickel-cobalt based alloys, and 20 stainless steel based alloys.

4. The canister of claim 1 wherein the fluid communication means comprises a port.

5. The canister of claim 4 wherein the port is covered by a re-sealable membrane.

6. The canister of claim 5 further comprising an extended tube is attached to the port.

7. The canister of claim 1 further comprising the interior chamber is configured to have internal raised channels.

8. The canister of claim 7 wherein the internal raised channels are continuous.

9. The canister of claim7 further comprising a plurality of internal baffles wherein the internal raised channels are separate from each other.

10. The canister of claim 1 wherein the interior chamber is divided into a plurality of separate and independent internal chambers.

11. The canister of claim 1 further comprising the nanoscale through- porous membrane morphology has a range between approximately 20 nm to 5000 nm, wherein nutrients, oxygen and metabolites are efficiently exchanged and supports canister vascularization when implanted.

12. An implantable canister for containing and delivering metabolically active agents, comprising:
    a metallic shell having nanoscale through-porous membrane characteristics including a bicontinuous morphology defining a first major surface, a second major surface, a side surface separating the first major surface and the second major surface, and an interior chamber between the first major surface and second major surface; and means allowing fluid communication with the interior chamber.

13. The canister of claim 12 wherein the metallic material is selected from the group consisting of cobalt-chromium based alloys, platinum alloys based, titanium alloys based, nickel-titanium based alloys, and stainless steel based alloys.

14. The canister of claim 12 wherein the fluid communication means comprises a port.

15. The canister of claim 14 wherein the port is covered by a re-sealable membrane.

16. The canister of claim 15 further comprising an extended tube is attached to the port.

17. The canister of claim 12 further comprising the interior chamber is configured to have internal channels.

18. The canister of claim 17 wherein the internal channels are continuous.

19. The canister of claim 17 further comprising a plurality of internal baffles wherein the internal channels are separate from each other.

* * * * *